(12) United States Patent
Bekker (10) Patent No.: US 8,296,982 B2
(45) Date of Patent: Oct. 30, 2012

(54) FORM FOR WRISTBAND WITH ADJACENT LABELS

(75) Inventor: Alexander Bekker, Sherman Oaks, CA (US)

(73) Assignee: Precision Dynamics Corporation, Valencia, CA (US)

( * ) Notice: Subject to any disclaimer, the term of this patent is extended or adjusted under 35 U.S.C. 154(b) by 262 days.

(21) Appl. No.: 12/616,289

(22) Filed: Nov. 11, 2009

(65) Prior Publication Data

US 2011/0107637 A1    May 12, 2011

(51) Int. Cl.
*A44C 5/00* (2006.01)

(52) U.S. Cl. .......................................... 40/633

(58) Field of Classification Search ................ 40/6, 633, 40/665; 283/75
See application file for complete search history.

(56) References Cited

U.S. PATENT DOCUMENTS

| | | |
|---|---|---|
| 3,698,383 A | 10/1972 | Baucom |
| 4,122,947 A | 10/1978 | Falla |
| 5,048,870 A | 9/1991 | Mangini et al. |
| 5,581,924 A | 12/1996 | Peterson |
| 5,979,941 A | 11/1999 | Mosher, Jr. et al. |
| 6,006,460 A * | 12/1999 | Blackmer ....................... 40/300 |
| 6,058,637 A * | 5/2000 | Duncan .......................... 40/633 |
| 6,179,337 B1 | 1/2001 | Zumberge |
| 7,240,446 B2 | 7/2007 | Bekker |
| 7,454,855 B2 | 11/2008 | Kotik et al. |
| 2007/0028495 A1 | 2/2007 | Kotik et al. |

* cited by examiner

*Primary Examiner* — Joanne Silbermann
(74) *Attorney, Agent, or Firm* — Kelly & Kelley, LLP (57) ABSTRACT

An improved identification band such as a wristband is provided with preprinted adhesive labels having a correlated unique identification code on the identification band and each of the labels. A label portion is separable from the wristband portion such that the wristband may be applied to a person or object to be identified. The label portion may be affixed to a specimen vial or other object to be identified as having a correlation with the person or object wearing the wristband. Individual labels are separable from the label portion, and the band portion in certain embodiments, so as to be applicable to other objects to be correlated to the person or object.

19 Claims, 6 Drawing Sheets

FORM FOR WRISTBAND WITH ADJACENT LABELS

BACKGROUND OF THE INVENTION

This invention relates generally to improvements in verification-identification band appliances such as wristbands and the like for mounting onto a specific person or object, and for carrying information associated with the specific wearer. More particularly, this invention relates to an improved verification-identification band incorporating primary and secondary identification zones in combination with a plurality of associated detachable or peel-off labels. The primary identification zone is capable of receiving wearer specific information at or near the time the verification-identification band is applied to the wearer. The secondary identification zone includes a pre-printed unique identifier code, which is also included on the associated labels to create a correlation between the band having the secondary identification zone and the detachable labels. The invention is particularly suited for use as a wristband or the like to be worn by a patient in a hospital or other medical facility, wherein patient information can be displayed on the primary identification zone at a convenient time such as at the time of patient admission or thereafter, with the labels being subsequently and individually separable on an as-needed basis for adherence to other objects associated with the patient, such as a vial containing a patient blood sample or the like. From this point forward, this description will refer to primarily to identification bands. Each occurrence of identification bands describes a device that performs not only an identification function, but a verification function as well.

Identification bands such as wristbands or bracelets and the like are commonly used to identify individual patients in a hospital or other medical facility. The identification band is normally imprinted with patient identification information such as patient name, room number, patient identification (ID) number, etc., and then secured about the patient's wrist or the like at the time of admission to the medical facility. Thereafter, in the course of patient treatment, the identification band is used to confirm and verify patient identity thereby insuring that each specific patient receives the appropriate treatment, pharmaceuticals, laboratory tests, surgical procedures, etc. In many instances, facility protocol will require transcribing of certain patient information onto other medical forms and/or objects such as specimen-containing vials and the like. Unfortunately, human transcription errors can still occur.

A variety of improved patient identification systems and methods have been developed in an attempt to provide improved correlation between a specific patient, and corresponding medical forms and laboratory specimens and related test results and the like. By way of illustrative example, a multi-part form has been provided to include a printable patient identification band such as a wristband, in combination with one or more printable adhesive labels, wherein the wristband and labels are concurrently imprinted with appropriate patient information, for example, at the time of patient admission to a medical facility. Further improvements include removable cards imprinted with the same information. The identification band is then detached from the multi-part form and secured to the associated patient. The related label and card portions of the multi-part form are then typically retained with the patient's chart or file, where the pre-printed labels and cards are available for individual detachment and affixation to subsequent medical forms, specimen vials and the like on an as-needed basis. See, for example, U.S. Pat. Nos. 4,122,947; 5,653,472; 6,067,739; 6,510,634; and 6,438,881; and co-pending U.S. Ser. No. 10/322,320.

While the above-described multi-part form system and method beneficially reduces or eliminates the opportunities for transcription errors, the detachable labels must be printed with identifying information at the same time as the wristband. There is also an inherent requirement to separate the pre-printed labels and cards from the patient identification band. As a result, when it is desired to affix one of the pre-printed labels onto a subsequent medical document or object, it is essential for medical personnel to retrieve and use a correct label associated with a specific patient. However, since medical personnel are commonly required to work concurrently with several patients at any given time, a significant opportunity remains for human error in connection with affixing an incorrect label or card associated with a different patient to medical documents and objects.

Another type of identification band to address this issues is a wristband including a series of detachable labels directly on the band. See, for example, U.S. Pat. Nos. 3,698,383; 7,481, 370 and 7,454,855. U.S. Pat. No. 7,454,855 describes a wristband having a plurality of detachable, pre-printed labels and cards as an extension or tail on the wristband. Because of the configuration of the system, the labels and cards interfere with the presentation of a plurality of wristbands as in an end-to-end series. In addition, the labels and cards must be removed from the wristband at the time it is attached to a person and placed in a file associated with the person without securement or attachment. Such separated labels may be lost or misplaced as they are used only when needed.

There exists, therefore, a continuing need for further improvements in and to patient verification-identification bands and associated label systems, for insuring substantially fail-safe affixation of a correct label or card associated with a specific patient to subsequent medical forms and documents, and related medical devices such as laboratory containers and the like. The present invention fulfills these needs and provides further related advantages.

SUMMARY OF THE INVENTION

The present invention is directed to an identification band, comprising an elongated flexible strap having a wristband portion and a label portion. The elongated flexible strap preferably defines a substantially rectangular structure.

The wristband portion has a primary identification zone, a secondary identification zone and a band portion. The primary and secondary identification zones are substantially co-extensive with the width of the flexible strap. The band portion is substantially less than the width of the flexible strap. The primary identification zone is configured to receive identification indicia. The secondary identification zone displays a unique identification code. The label portion is disposed adjacent to and substantially co-extensive with the length of the band portion and has a plurality of detachable labels. The label portion is substantially less than the width of the flexible strap and each of the labels displays the unique identification code. The band portion may also have a plurality of detachable labels, which each display the unique identification code.

The band and label portions are offset from a centerline of the flexible strap such that a junction between the band portion and the label portion approximates the centerline. The adjacent label and band portions, as a whole, are substantially co-extensive with the width of the flexible strap. The junction between the band portion and the label portion comprises a score line, a line of weakness or a perforation line along the centerline or their common sides such that the label portion is separable from the band portion.

The wristband portion is configured to form a closed loop through the use of a closure mechanism disposed at a first end of the flexible strap and configured to receive the band portion. The closure mechanism may comprise an adhesive closure, a snap closure, or another closure mechanism known in the art. The label portion has an attachment mechanism disposed at an end thereof, preferably a second end of the flexible strap. The attachment mechanism is configured to attach the label portion to an article related to a specific wearer or object, such as a specimen vial or other medical container. The labels may then be removed from the label portion for applying to a medical form or other object to be associated with the patient.

The primary identification zone is configured to receive the identification indicia by hand-writing, printing or a pre-printed tag/label. The pre-printed tag/label is configured to adhere to the primary identification zone, be disposed under an adhesive transparent cover film on the primary identification zone, or inserted into a clear window on the primary identification zone. Such methods of applying identification indicia to an identification zone are known in the art and readily understood by those skilled in the art.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

As shown in the exemplary drawings, an improved identification band referred to generally in FIGS. 1-6 by the reference numeral 10 is provided for mounting onto a specific person or object, such as a wristband for mounting onto the wrist of a patient in a medical facility or the like. The identification band 10 is an elongated flexible strap incorporating a wristband portion 12 and a label portion 14. The identification band 10 has a substantially rectangular structure such that the wristband portion 12 and label portion 14 when joined together generally define a rectangle.

The wristband portion 12 preferably includes a primary identification zone 16, a secondary identification zone 18 and a band portion 20. The primary identification zone 16 and secondary identification zone 18 are substantially coextensive with the width of the identification band 10. The primary identification zone 16 is configured to receive identification indicia 22 regarding the person or object on which the identification band 10 is mounted. The secondary identification zone 18 preferably displays a unique identification code 24. Because the primary and secondary identification zone 16,18 are permanently affixed to the identification band 10, a correlation is created between the identification indicia 22 applied to the primary identification zone 16 and the unique identification code 24 pre-printed on the secondary identification zone 18. As described more fully below, this correlation extends to the detachable labels 26 on the label portion 14, each of which include the same unique identification code 24.

Figure 1:
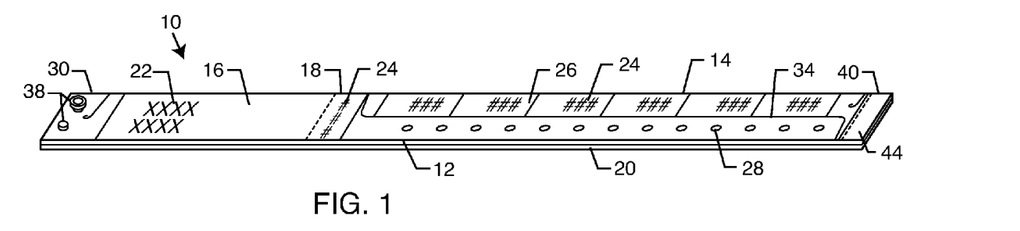
FIG. 1 is a perspective view illustrating an identification band of the present invention.
Figure 2:
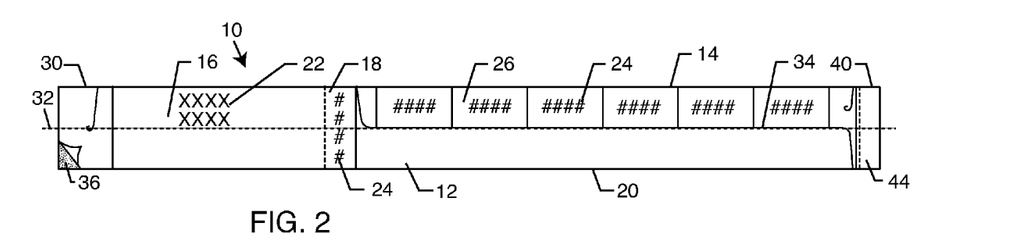
FIG. 2 is a top plan view illustrating an identification band of the present invention.
Figure 3:
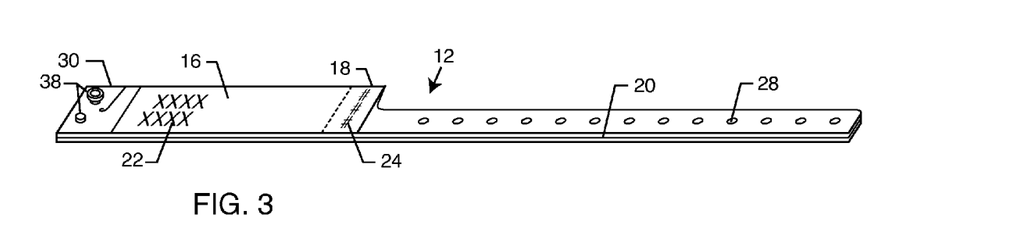
FIG. 3 a perspective view illustrating an identification band of the present invention with the label portion removed.
Figure 4:
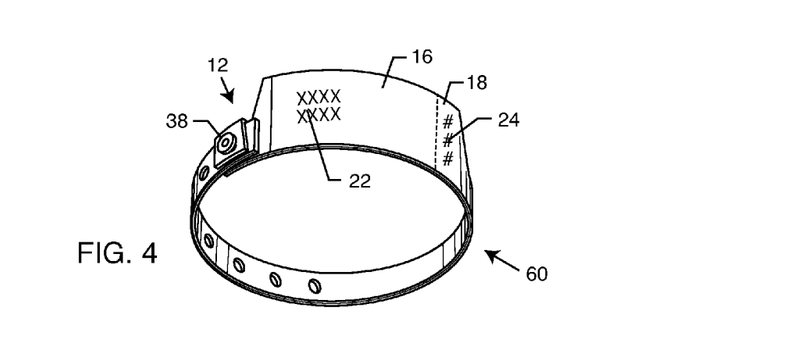
FIG. 4 is a perspective view of the identification band of FIG. 6 formed into a closed loop.

The band portion 20 preferably includes a closure mechanism 30 disposed on one end of the identification band 10, which may comprise either an adhesive closure 36 (FIG. 2) or a snap closure 38 (FIG. 1). The adhesive closure 36 includes a removable liner and an underlying adhesive layer that can be used to secure the band portion 20 in a closed loop configuration (FIG. 4). The snap closure 38 preferably includes plastic components which engage one of a series of openings 28 or other structures on the band portion 20 to cooperate with the snap closure mechanism 38. Such adhesive closures 36 or snap closures 38 are known in the art. The band portion 20 and label portion 14 are offset from a centerline 32 of the identification band 10 such that the junction between the band portion 20 and label portion 14 approximates the position of the centerline 32. This junction between the band portion 20 and label portion 14 preferably comprises a score line, perforation line or line of weakness 34 such that the label portion 14 is separable from the band portion 20.

The label portion 14 preferably comprises a plurality of detachable labels 26. The label portion 14 is disposed adjacent to and substantially coextensive with the length of the band portion 20. The band portion 20 and the label portion 14 are both substantially less than the width of the identification band 10. The combined width of the band portion 20 and label portion 14 is substantially coextensive with the width of the identification band 10. The labels 26 each display the unique identification code 24 that is displayed in the secondary identification zone 18.

Figure 10:
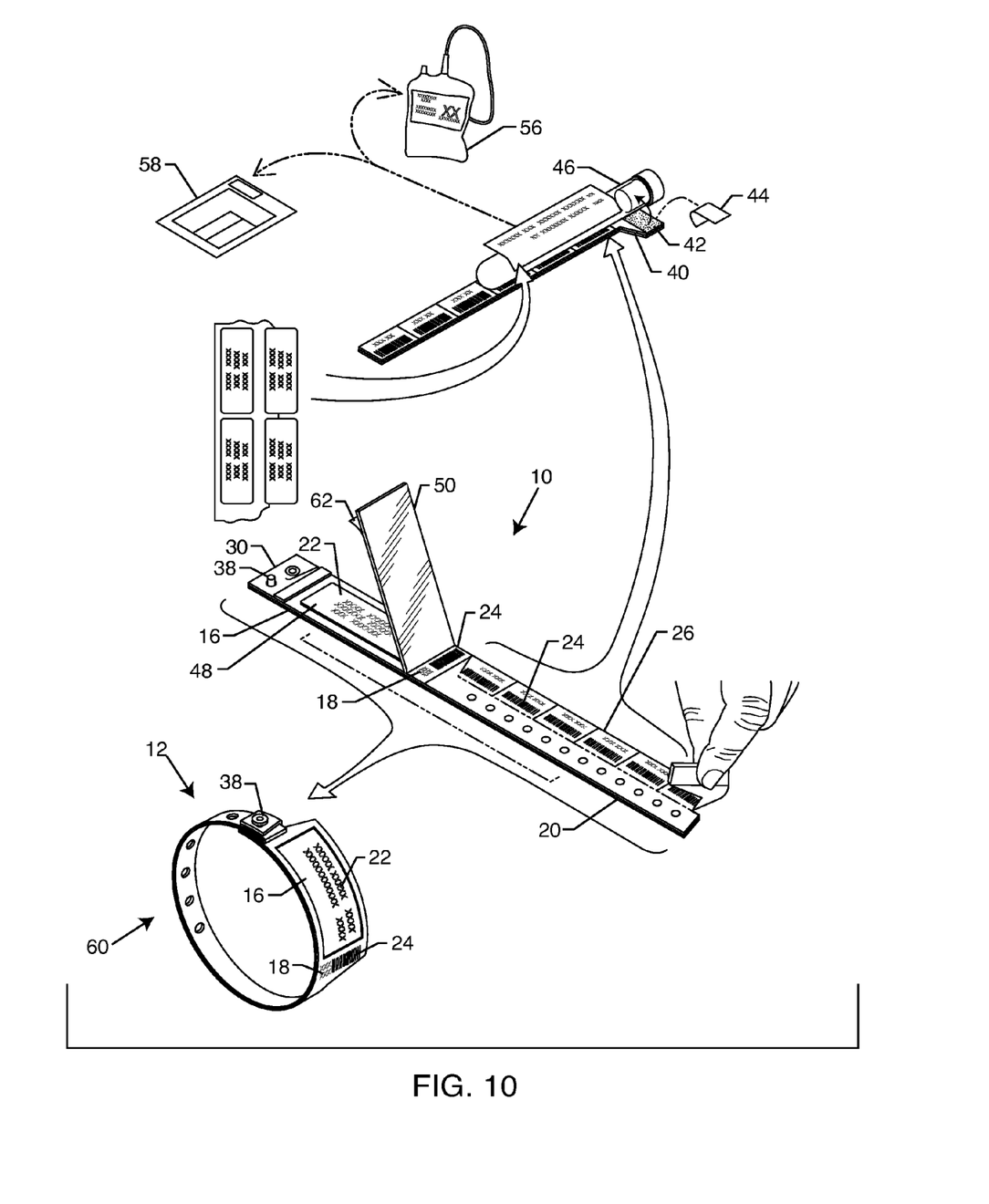
FIG. 10 is an illustration of a method of use of an identification band of the present invention having a protective shield in the primary identification zone for receiving a printed label.
Figure 11:
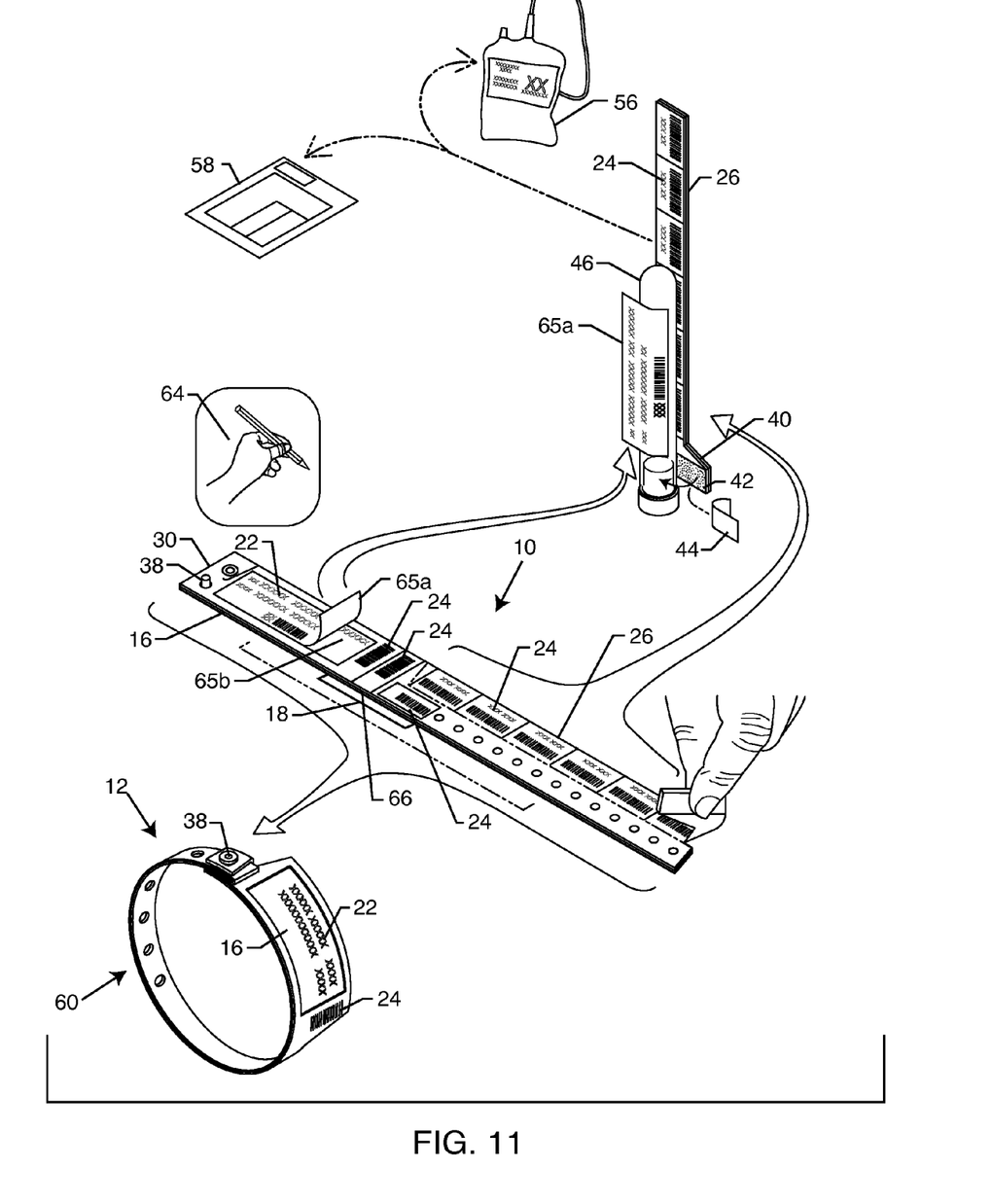
FIG. 11 is an illustration of another method of use of an identification band of the present invention having an imaging liner in the identification zone for receiving handwritten information.

The label portion 14 preferably includes an attachment mechanism 40 to secure the label portion 14 to a specimen vial 46 or similar object to be associated with the specific person or object wearing the identification band 10. The attachment mechanism 40 preferably includes an adhesive layer 42 covered by a release layer 44. Once the release layer 44 is removed, the adhesive layer 42 is exposed and may be adhered to the outer surface of a specimen vial 46 as illustrated in FIGS. 10 and 11. In this way, the label portion 14 is used upon separation from the identification band 10, reducing the chance of it being lost or misplaced if it is simply placed in the patient's medical file.

The primary identification zone 16 is configured to receive identifying indicia 22 by handwriting, printing or applying a pre-printed label/tag. The preprinted label/tag 48 is configured to adhere to the primary identification zone 16, be disposed under an adhesive transparent cover film 50 or inserted into a clear window 52. A person having ordinary skill in the art will be familiar with methods of using a preprinted label/tag 48, a transparent cover film 50 or a clear window or pocket. Such structures are known and disclosed in U.S. Pat. Nos. 5,581,924 and 7,240,446. In addition, United States published application number 2007/0028495 also discloses such structures.

Figure 5:
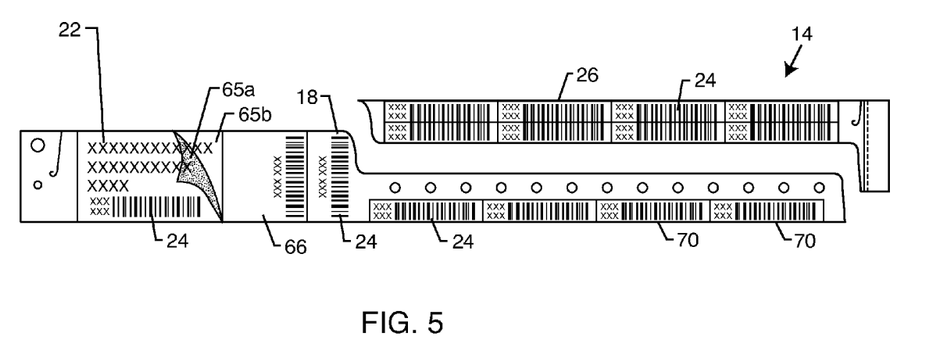
FIG. 5 is a top plan view illustrating an alternate embodiment of the inventive identification band.
Figure 6:
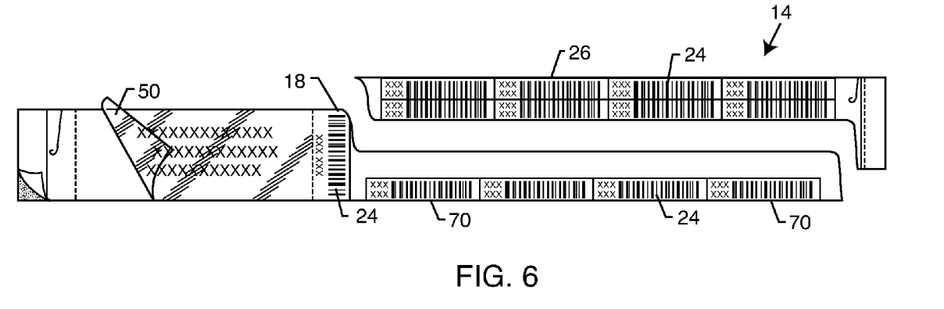
FIG. 6 is a top plan view illustrating another alternate embodiment of the inventive identification band.

FIGS. 5 and 6 illustrate alternate embodiments of the identification band 10. In both embodiments the bands 10 are constructions substantially as described above. However, FIGS. 5 and 6 illustrate an embodiment that includes an additional series of detachable labels 70 in the band portion 12. These detachable labels 70 include the same unique identification code 24 as is displayed in the secondary identification zone 18 and the detachable labels 26 on the label portion 14. This provides another set of detachable labels 70 that stay with the patient rather than being placed in the medical file, on a specimen vial or another location where they may be misplaced or mistakenly used. FIG. 5 also shows the snap closure mechanism 38 described above and the imaging liner 65a, 65b for the primary identification zone 16 described below. FIG. 6 shows the adhesive closure mechanism 36 described above and the protective shield 50 for the primary identification zone 16 described below.

Figure 7:
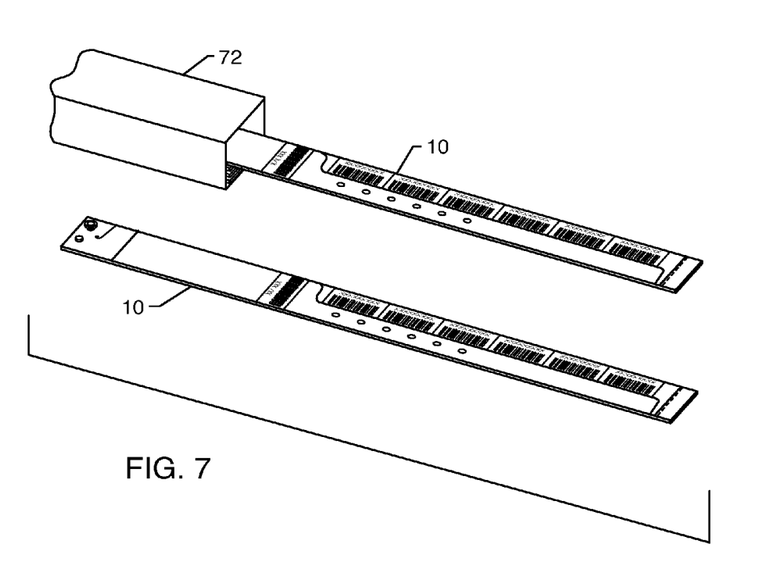
FIG. 7 is a perspective view of a plurality of inventive identification bands presented in a single band dispenser box.
Figure 8:
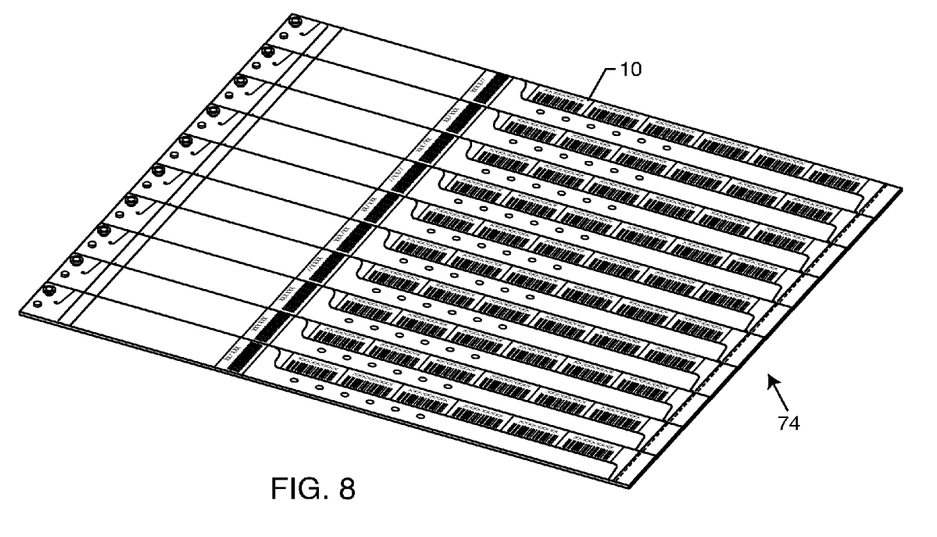
FIG. 8 is a perspective view of a plurality of inventive identification bands presented in a sheeted form.
Figure 9:
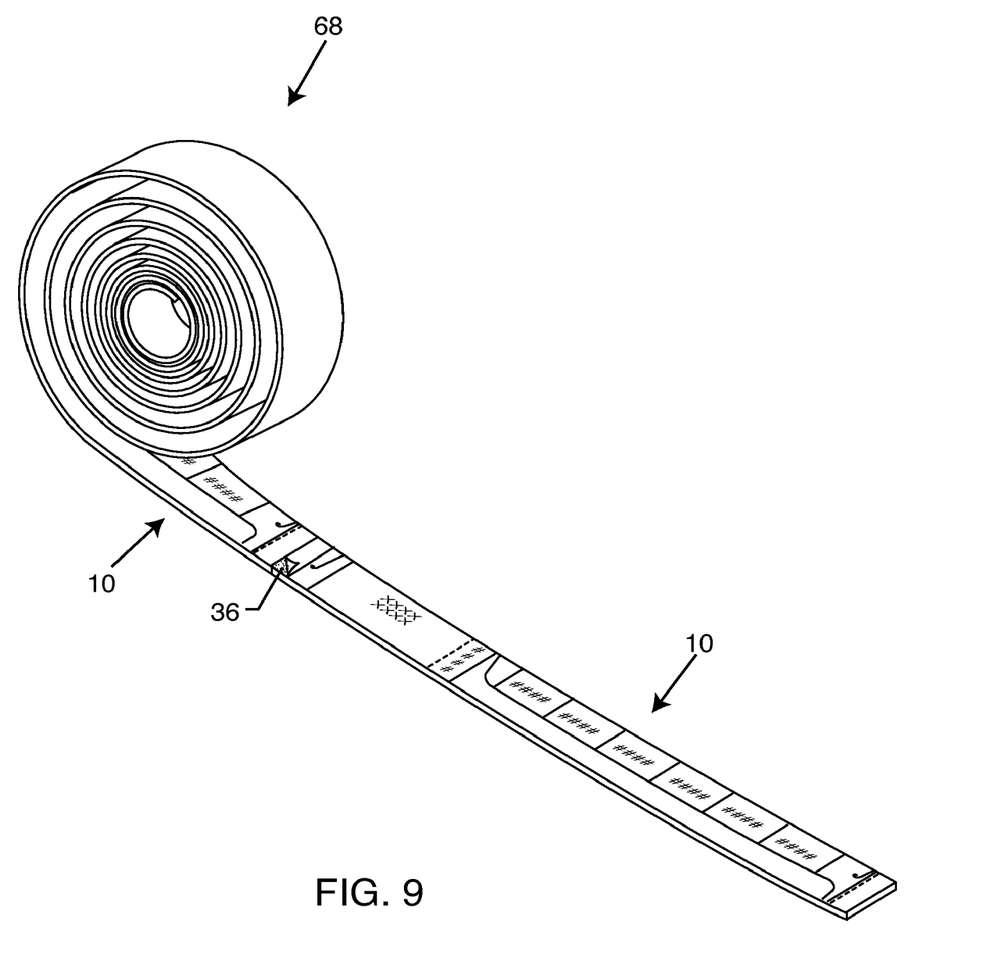
FIG. 9 is a perspective view of a plurality of inventive identification bands presented in a roll form.

Because the identification band 10 has a generally rectangular structure and the label portion 14 is substantially coextensive with the band portion 20 it is possible to provide a plurality of identification bands 10 in multiple formats. FIG. 7 illustrates the presentation of a plurality of identification bands 10 in an individual form from a dispenser box 72 or similar structure. FIG. 8 illustrates the presentation of a plurality of identification bands 10 in a sheet form 74. FIG. 9 illustrates the presentation of a plurality of identification bands 10 connected end-to-end in the form of a roll 68. Prior art identification bands that included correlated adhesive labels such as this disposed the labels as a continuation of the wristband such that the labels were an extension of the wristband. Such construction would make providing a plurality of identification bands 10 in an end-to-end configuration unmanageable and difficult. The substantially coextensive construction of the label portion 14 and band portion 20 facilitates providing a plurality of identification bands 10 in an end-to-end series as described herein.

FIGS. 10 and 11 illustrate preferred methods of using the identification band 10 of the present invention. In both methods, the label portion 14 is separated from the identification band 10 along the score line 34. The label portion 14 may then be adhered to a specimen vial 46 or similar object. The label portion 14 is adhered to the specimen vial 46 by removal of the release layer 44 from the adhesive layer 42 such that the attachment mechanism 40 may be wrapped around the exterior of the specimen vial 46, thus securing the label portion 14 to the specimen vial 46. Individual labels 26 may then be removed from the label portion 14 as affixed to the specimen vial 46 and used to correlate the same to other objects such as blood bags 56 or patient charts 58.

The wristband portion 12 may then be formed into a closed loop 60 around the person or object to be identified. The closure mechanism 30 affixed adjacent to the primary identification zone 16 may then engage the openings 28 on the band portion 20 to secure the wristband portion 12 in the closed loop 60.

As described above, the primary identification zone 16 may comprise a transparent cover film 50 which is releasable at one end from the wristband portion 12 to allow identifying indicia 22 to be applied to the primary identification zone 16. As depicted in FIG. 10, the transparent cover film 50 has a release layer 62 which when removed exposes an adhesive layer (not shown) to secure the transparent cover film 50 to the primary identification zone 16. Alternatively, the primary identification zone 16 may accept a preprinted tag 48 or hand/machine printed information 64. Alternatively, the primary identification zone 16 may comprise a multi-layer imaging liner 65a, 65b that receives handwritten information 22 on the upper layer 65a. The under layer 65b is configured to create a copy of the information 22 in response to the pressure exerted on the upper layer 65a during handwriting. The upper layer 65a is then removable and may be adhered to a specimen vial 46 or other object to be associated with the patient such as a chart 58 or a blood bag 56.

The secondary identification zone 18 may present the unique identification code 24 in only one place on the wristband portion 12 as depicted in FIG. 10. Alternatively, the secondary identification zone 18 may include multiple occurrences of the unique identification code 24 as depicted in FIG. 11. One or more of these occurrences of the unique identification code 24 in the secondary identification zone 18 may comprise a removable label or tag 66 which may be applied to objects requiring correlation to the wristband 12 as the labels 26 discussed above.

Although several embodiments have been described in detail for purposes of illustration, various modifications may be made without departing from the scope and spirit of the invention. Accordingly, the invention is not to be limited, except as by the appended claims.

What is claimed is:

1. An identification band, comprising:
   an elongated flexible strap consisting of a wristband portion and a label portion;
   the wristband portion consisting of a wristband, said wristband consisting of a primary identification zone, a secondary identification zone and a band portion, wherein the primary and secondary identification zones are each substantially co-extensive with the width of the flexible strap and the band portion is substantially less than the width of the flexible strap, and wherein the primary identification zone is configured to receive identification indicia and the secondary identification zone displays a unique identification code; and
   the label portion being disposed immediately adjacent to and substantially co-extensive with the length of the band portion and consisting of a plurality of detachable labels, wherein the label portion is substantially less than the width of the flexible strap and each of the labels displays the unique identification code.

2. The identification band of claim 1, wherein the band and label portions are offset from a centerline of the flexible strap such that a junction between the band portion and the label portion approximates the centerline.

3. The identification band of claim 2, wherein the adjacent label and band portions together are substantially co-extensive with the width of the flexible strap.

4. The identification band of claim 2, wherein the junction between the band portion and the label portion comprises a line of weakness such that the label portion is separable from the band portion.

5. The identification band of claim 1, wherein the wristband portion is configured to form a closed loop.

6. The identification band of claim 5, wherein the wristband portion has a closure mechanism adjacent to the primary identification zone, disposed at a first end of the flexible strap and configured to receive the band portion.

7. The identification band of claim 6, wherein the closure mechanism comprises an adhesive closure or a snap closure.

8. The identification band of claim 6, wherein the label portion has an attachment mechanism disposed at a second end of the flexible strap and configured to attach the label portion to an article related to a specific wearer or object.

9. The identification band of claim 1, wherein the primary identification zone is configured to receive the identification indicia by hand-writing, printing or a pre-printed tag.

10. The identification band of claim 9, wherein the pre-printed tag is configured to adhere to the primary identification zone, be disposed under an adhesive transparent cover film on the primary identification zone, or inserted into a clear window on the primary identification zone.

11. The identification band of claim 1, wherein the elongated flexible strap defines a substantially rectangular structure.

12. An identification band, comprising:
    an elongated flexible strap defining a substantially rectangular structure consisting of a wristband portion and a label portion;
    the wristband portion consisting of a wristband, said wristband consisting of a primary identification zone, a secondary identification zone and a band portion, wherein the primary and secondary identification zones are each substantially co-extensive with the width of the flexible strap and the band portion is substantially less than the width of and offset from a centerline of the flexible strap, and wherein the primary identification zone is configured to receive identification indicia and the secondary identification zone displays a unique identification code;
    the label portion being disposed immediately adjacent to and substantially co-extensive with the length of the band portion and consisting of a plurality of detachable labels, wherein the label portion is substantially less than the width of and offset from a centerline of the flexible strap and each of the labels displays the unique identification code; and
    wherein the adjacent label and band portions together are substantially co-extensive with the width of the flexible strap and a junction between the band portion and the label portion approximates the centerline of the flexible strap.

13. The identification band of claim 12, wherein the junction between the band portion and the label portion comprises a line of weakness such that the label portion is separable from the band portion.

14. The identification band of claim 12, wherein the wristband portion is configured to form a closed loop.

15. The identification band of claim 14, wherein the wristband portion has a closure mechanism adjacent to the primary identification zone, disposed at a first end of the flexible strap and configured to receive the band portion.

16. The identification band of claim 15, wherein the closure mechanism comprises an adhesive closure or a snap closure.

17. The identification band of claim 15, wherein the label portion has an attachment mechanism disposed at a second end of the flexible strap and configured to attach the label portion to an article related to a specific wearer or object.

18. The identification band of claim 12, wherein the primary identification zone is configured to receive the identification indicia by hand-writing, printing or a pre-printed tag.

19. The identification band of claim 18, wherein the pre-printed tag is configured to adhere to the primary identification zone, be disposed under an adhesive transparent cover film on the primary identification zone, or inserted into a clear window on the primary identification zone.

* * * * *